United States Patent [19]
Ozero

[11] Patent Number: 4,879,396
[45] Date of Patent: Nov. 7, 1989

[54] SELECTIVE EXTRACTION OF $CO_2$ AND ARGON FROM ETHYLENE OXIDE RECYCLE SYSTEM

[75] Inventor: Brian J. Ozero, New York, N.Y.

[73] Assignee: Scientific Design Company, Inc., Little Ferry, N.J.

[21] Appl. No.: 22,498

[22] Filed: Mar. 6, 1987

Related U.S. Application Data

[63] Continuation of Ser. No. 729,340, May 1, 1985, abandoned.

[51] Int. Cl.4 .......................................... C07D 301/10
[52] U.S. Cl. ................................................... 549/534
[58] Field of Search ......................................... 549/534

[56] References Cited

U.S. PATENT DOCUMENTS

| | | | |
|---|---|---|---|
| 3,083,213 | 3/1963 | Courter | 549/534 |
| 3,119,837 | 1/1964 | Kingsley et al. | 549/534 |
| 3,725,307 | 4/1973 | Brown et al. | 549/534 |
| 4,230,463 | 10/1980 | Henis et al. | 55/16 |

FOREIGN PATENT DOCUMENTS

| | | | |
|---|---|---|---|
| 1055147 | 1/1967 | United Kingdom | 549/534 |
| 1191983 | 5/1970 | United Kingdom | 549/534 |
| 1321095 | 6/1973 | United Kingdom | 549/534 |

OTHER PUBLICATIONS

R. P. Rastogi et al., *J. of Membrane Science* (1978), "Thermoosmotic Studies on Argon Gas and Binary Gas Mixtures of . . . ", 4, 1–15.

W. A. Bollinger et al., CEP (1982), "Separating Systems for Oil Refining and Production", pp. 27–32.

R. S. Narayon et al., Paper Presented at the Permian Basin Regional Meeting of Gas Processors Association, May 6, 1982, Midland, Texas, 1–18.

*Primary Examiner*—Richard L. Raymond
*Assistant Examiner*—Mark W. Russell
*Attorney, Agent, or Firm*—Kenneth H. Johnson

[57] ABSTRACT

An improved process is disclosed for producing ethylene oxide; the process utilizing suitable semipermeable membrane units to selectively remove desired amounts of both carbon dioxide and argon diluents from the reaction recycle gas. The utilization of such a process makes possible to utilize a much cheaper low purity oxygen source without concern for feed purge losses.

1 Claim, 1 Drawing Sheet

SELECTIVE EXTRACTION OF CO$_2$ AND ARGON FROM ETHYLENE OXIDE RECYCLE SYSTEM

This application is a continuation, now abandoned, of application Ser. No. 729,340, filed 05/01/85 now abandoned.

BACKGROUND OF THE INVENTION

1. Field of the Invention

This invention relates to an improvement in the process for the production of ethylene oxide through the silver catalyzed vapor phase oxidation of ethylene and, more particularly, relates to an economic process for producing ethylene oxide which utilizes suitable semipermeable membrane separation units, permits the usage of a cheap, low purity oxygen feedstock, and minimizes the unreacted ethylene losses by a selective removal of argon and CO$_2$ diluents from the process recycle gas stream.

2. Description of the Prior Art

The production of ethylene oxide is one of the most important commercial reactions in the world, with a current annual production of about eight million tons/year worldwide. Frequently the operation of a process of this magnitude within the realm of commercial practicality can often depend upon the ability to increase, even by only relatively small amounts, the ethylene oxide yield or, conversely, the ability to reduce, even by only relatively small amounts, the costs of a variety of essential elements in the process.

In one major embodiment of the process, the oxygen supplied for reacting with ethylene is obtained either from an expensive oxygen source providing essential relatively pure oxygen, i.e., at least, 95+%, or, alternatively, a cheaper, less pure stream supplying primarily molecular oxygen, along with a lesser but significant fraction of one or more diluents, e.g., nitrogen, argon and the like. Such a second source of oxygen can be obtained, for example, from air treated by suitable separation processes (Pressure Swing Adsorption), typically creating a gas having an oxygen content of about 90 mole %, or less. When added to the process cycle gas, usually in conjunction with a makeup ethylene feed, the oxygen and ethylene become mixed with a controlled amount of other diluents, other reaction products and contaminants, as for example, carbon dioxide, argon, nitrogen, methane, etc. The precise number and concentration of each ingredient which can be included is a significant consideration in forming a desirable reaction gas composition, since, among other considerations, one must avoid a composition having very high and unstable concentrations of oxygen and/or ethylene. Otherwise, a total combustion of the ethylene content, as well as the danger of an explosion caused by exceeding the flammability limit of the gas composition, can take place. CO$_2$ is a particularly important diluent, since it is the major byproduct of the vapor phase process forming ethylene oxide. Depending on the reactor feed composition, catalyst type, age, etc., the process results in the production of 0.4–1.0 moles of CO$_2$ per mole of ethylene oxide. Thus, a method of selectively monitoring and economically removing excess CO$_2$, and other excess amount of impurities such as argon, while avoiding a substantial loss in reactant gas, particularly ethylene, has been a long felt need in the art.

In large scale plants currently in use, excess CO$_2$ is usually chemically absorbed from the reaction recycle gas by contacting it with a hot potassium carbonate solution, stripping it out using steam, and vented into the atmosphere with a minimal loss of ethylene. However, such absorption units are quite expensive, and also require substantial amounts of energy during utilization; consequently in smaller size commercial plants which are unable to afford such expensive units the art has been forced to use a less expensive, and much less selective CO$_2$ purge system which vents a substantial amount of ethylene along with the excess CO$_2$. It is only when the economies of scale produced by large plants can be obtained does the expensive carbonate chemical absorption system, its use saving substantial amounts of ethylene purge losses, become truly feasible.

U.S. Pat. No. 3,083,213 is an early teaching on the undesirability of the presence of argon, particularly regarding the flammability issue, in a disclosed ethylene oxide process. In commercial ethylene oxide systems the art has controlled the argon level in the recycle gas by a venting, or bleeding mechanism, which of course, also results in the loss of a substantial amount of ethylene, resulting in a reduced ethylene oxide yield. U.S. Pat. No. 3,119,837 discloses that methane can be a suitable diluent under certain circumstances in an ethylene oxide process. British Pat. No. 1,321,095 discloses an ethylene oxide process wherein ethylene levels as high as 40–80% by volume are permitted, and in which several diluents are controlled through means of a vent mechanism.

The usage of membranes to separate a wide variety of gaseous components has become increasingly important in recent years, although its usage is still believed unknown in the ethylene oxide art. In copending case Ser. No. 729,431, of Brian Ozero, filed concurrently with the present application, the usage of semipermeable membranes to selectively purge argon from a fraction of an ethylene oxide recycle gas stream is disclosed; the process utilizing a high purity oxygen feed stream and a hot carbonate system for the great majority of the CO$_2$ removal.

It is, therefore, an object of this invention to provide a process for the selective one-step removal of CO$_2$ and argon from the ethylene-oxygen recycle gas mixture.

It is another object of this invention to provide a process for the removal of CO$_2$ and argon, along with the maintaining of a desired recycle gas composition, without an accompanying substantial loss of ethylene, in the ethylene-oxygen recycle gas.

It is still another object of this invention to provide process for the economic, semipermeable membrane assisted removal of CO$_2$ and argon from the recycle gas in conjunction with the usage of a low-purity oxygen feedstock, in an ethylene oxide process.

SUMMARY OF THE INVENTION

Accordingly, the invention comprises an improved process for the production of ethylene oxide, comprising reacting ethylene with, preferably, oxygen supplied from a low purity oxygen source, e.g., an O$_2$ source containing about 75 to 95 mole % O$_2$, and most preferably, about 90 mole % O$_2$, such as that supplied from a Pressure Swing Adsorption (PSA) unit; in the presence of a suitable silver-based catalyst under suitable elevated temperatures, preferably about 200–300° C., and super-atmospheric pressures, preferably about 150–350 psia; the reaction occurring in the further presence of a suitable reaction gas mixture, i.e., about 5 to 30 mole % ethylene, 5 to 9 mole % O$_2$, 1 to 25 mole % Ar, 5 to 25 mole % $CO_2$, 0.2 to 1.0 mole % $H_2O$, and 25 to 70 mole % combined amount of $CH_4$ and $N_2$; removing the ethylene oxide product from the reaction gas mixture, e.g., in a suitable scrubbing zone; further removing a desired amount of both $CO_2$ and argon from the reaction gas mixture by passing a suitable amount of the ethylene oxide-free reaction gas effluent, e.g., about 20 to 100%, preferably from 50 to 100%, through a suitable semipermeable membrane unit; i.e., a semipermeable membrane unit maintained at a pressure differential of about 20 to 400 psi, preferably about 100 to 250 psi; the average rate of $CO_2$ removal from the reaction gas mixture being substantially equal to the average rate of $CO_2$ formed in the gas mixture during the reaction cycle, and the average rate of argon removal from the reaction gas mixture being substantially equal to the average rate of argon entering the gas mixture during the reaction cycle from the low purity oxygen feed source; replenishing the depleted reactant gases, i.e., $O_2$ and $C_2H_4$, with fresh feed, and repeating the process cycle.

DETAILED DESCRIPTION OF THE INVENTION

Figure 1:
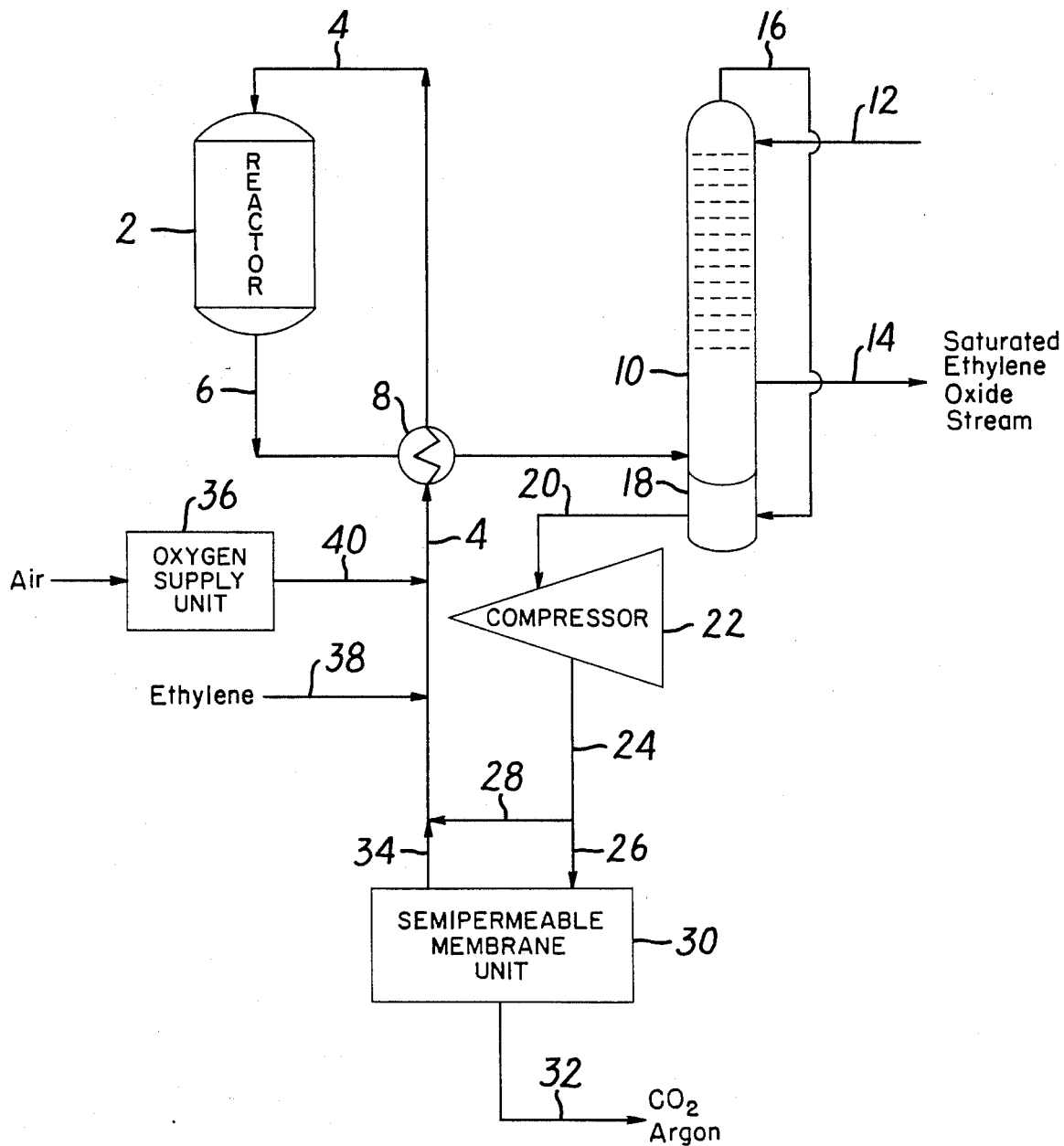
FIG. 1 sets forth a brief outline of the preferred process of the invention described.

Ethylene oxide today is produced commercially through the silver catalyzed, vapor phase incomplete oxidation of ethylene by molecular oxygen. Typically, the product ethylene oxide generally constitutes but a relatively small percentage of the total effluent stream leaving the oxidation reaction zone, e.g., about 1 to 3 mole %. The remainder of the reactor effluent comprises several diluents and reaction byproducts; the diluents functioning to negate the possibility of explosions and unwanted combustibility levels being attained during the reaction. If the so-called flammability limit, i.e., at which point the complete and rapid oxidation of ethylene to $CO_2$ and water can occur, is exceeded, the possibility of a serious explosion becomes a very real factor. Naturally, it is desired to operate under conditions which will maximize the conversion of ethylene to ethylene oxide, yet avoid safety problems while maintaining an industrially acceptable reaction rate. In an effort to find such an optimum environment, gases such as nitrogen and methane are intentionally introduced and along with the reaction byproduct carbon dioxide, and argon, which enters as an impurity in the oxygen feed, are maintained at predetermined concentrations in the recycle reaction gas. The goal of such composition setting is to find an optimum mixture which permits one to safely react maximum concentrations of oxygen and ethylene, thereby also increasing the selectivity of the ethylene present in the reaction to form ethylene oxide.

Some of the diluents present in the recycle gas owe their origin to a gradual accumulation of impurities which are present in the reactant gas feed streams. This is certainly the case with argon, which enters the system as the major impurity present in the oxygen feed stream. The art has been unable to find a selective manner of removing the excess argon which builds up in the system, other than by simply purging a predetermined amount of the recycle gas mixture escape through a bleed stream which is then discarded. Such a purge gas, unfortunately, also contains a high ethylene concentration and results in a substantial ethylene loss, e.g., from about 0.1 to 5.0 mole % of the mixture, the magnitude of which depends on the argon content in the oxygen feed and the recycle gas stream.

The amount of $CO_2$ present in the recycle gas mixture, and the maintenance of this concentration within desired levels, is of even greater importance than maintaining a desired argon concentration, since $CO_2$ is formed in significant amounts as a byproduct of the ethylene oxide forming reaction.

Surprisingly, I have discovered that the incorporation of a suitable semipermeable membrane unit, e.g., either a single unit or multi-stage membrane configuration, with a typical separator unit installed in a pressure vessel in a manner analogous to a shell and tube heat exchanger, can efficiently and selectively extract both the $CO_2$ and the argon from the remaining recycle mixture. The feed gas, i.e, a desired amount of the recycle gas stream, is first fed into the shell side of the separator. Due to the presence of a significant pressure differential, e.g., from about 20 to 400 psi, preferably from about 100 to 250 psi, between the outer and inner sides of the membrane tube of fibres, the component or components desired to be separated more easily permeates through the membrane film than the other components as the gas stream traverses the length of the bundle. The resultant selective separation yields a permeate stream with significantly higher $CO_2$ to ethylene, and argon to ethylene mole ratios on the inner side of the membrane tube or fibre than in the nonpermeate stream, which is ethylene-rich, on the shell side. The relative rate of permeation of each component present in the gas mixture is, in general, a function of the individual component's partial pressure differential across the fibre wall, as well as the component's solubility and diffusivity in the fibre. A preferred semipermeable membrane for use in the process is that sold under the trade name "PRISM" by Monsanto Company, St. Louis, MO, but a wide variety of other such semipermeable membrane units, as will be apparent to one skilled in the membrane art, are within the scope of the invention.

The process of the invention is of the type in which inexpensive, low-purity oxygen, such as is supplied by a PSA plant, is preferably employed as a feedstock to replenish the oxygen consumed in the reaction. Preferably, the feed oxygen possesses an oxygen content of about 90 mole %, and is introduced as a makeup stream into the system, typically being present in purity ranging from about 75 to 95 mole % $O_2$. It is also desirable to operate in the range of high ethylene concentrations in order to achieve a high ethylene selectivity to ethylene oxide as this is clearly essential for commercial operation, and thus ethylene concentrations as high as about 30 mole % can be present in the recycle gas mixture.

The gas mixture comprising the recycle reaction gas stream, in addition to the feed gases and the different impurities, also contains significant amounts of certain reaction products, e.g., the $CO_2$ formed as a major byproduct which has not been removed, water, and a small amount of unremoved ethylene oxide.

FIG. 1 sets forth a simplified outline of the preferred embodiment of the process. The system comprises a reactor unit 2 containing a suitable silver metal-based catalyst known to those in the art, e.g., such as that disclosed in U.S. Pat. No. 3,725,307, as well as many others, and through which an ethylene and oxygen-containing mixture, entering through line 4 is passed, with fresh makeup ethylene and oxygen having been introduced earlier into line 4. A reactor effluent stream comprising ethylene oxide, unreacted feed components, various diluents and reaction byproducts is withdrawn from reactor unit 2 through line 6 and, after preferably being cooled in heat exchanger 8, preferably by warming the incoming reactor feed mixture in line 4, passes into a scrubbing unit (or other suitable separation unit) 10 wherein the gas mixture is scrubbed by contacting with an aqueous stream or another suitable ethylene oxide scrubbing agent entering through line 12, eventually leaving the unit containing the absorbed ethylene oxide through line 14; from which stream the ethylene oxide is eventually extracted therefrom as product. The ethylene oxide-free effluent passes out of the scrubber through line 16 and passes through a mist separator 18 which removes any entrained liquid present. The scrubbed gas from separator 18 passes through line 20, and enters a compressor unit 22, where it is raised to a desired elevated pressure, e.g., about 200-340 psia. The pressurized gas stream, typically containing about 1-25% Ar, preferably 3-15% Ar, and about 5-25% $CO_2$, preferably 5-20% $CO_2$, passes through line 24 and is divided into two sections, with about 20-100%, preferably 50-100%, passing through line 26 and entering into semipermeable membrane unit 30, while the remaining recycle gas passes through bypass line 28.

In membrane unit 30, a preferred design of which has been described earlier herein, a small permeate stream, e.g., about 0.3-3.0% of the pressurized gas stream present in line 24 is withdrawn from the membrane unit via line 32. Stream 32 typically removes about 3-25% of the $CO_2$ and 0.4-4.0% of the argon present in the recycle gas mixture (stream 24). The surprising effective separation is due to the unexpected selective separation properties exhibited by membranes towards removing not only $CO_2$, but also argon, from the recycle gas composition. After its separation the $CO_2$/argon-rich stream exits the membrane unit through line 32, typically either being vented or passed to an incinerator, or the like. The treated, $CO_2$/argon leaner stream exits the membrane unit in line 34, is combined with the bypass stream 28, and is then replenished by fresh ethylene and oxygen makeup streams 38 and 40, respectively. The oxygen makeup stream is preferably supplied from an inexpensive source of low purity oxygen, such as Pressure Swing Adsorption unit 36, i.e., a unit which utilizes molecular sieves to absorb most of the nitrogen present in the air thereby producing a low cost oxygen with a high argon content, typically about 5 mole %, and also containing about 5% nitrogen as the oxygen feedstock.

Normally the high argon content in PSA or another low purity oxygen would necessitate a substantial loss of ethylene in the large cycle gas purge stream which would have to be vented in order to limit an undesirable buildup of argon. Surprisingly, however, when semipermeable membranes are utilized for $CO_2$ removal, instead of the conventional hot carbonate process, a low cost, low purity oxygen such as supplied from a PSA unit can be substituted for the more costly, high purity oxygen supplied from cryogenic air separation units, and the like, without any increase at all in ethylene purge losses beyond that necessitated by the $CO_2$ purge itself. Such an improvement naturally produces a substantial economic savings. While semipermeable membranes are not economically suitable to remove $CO_2$ in medium to large commercial ethylene oxide plants due to the significant losses of expensive ethylene necessitated by their use (as opposed to the installation of a suitable hot carbonate system), in small ethylene oxide plants the aforementioned membrane separation unit is more economically suitable than the expensive carbonate system which needs the aforementioned economies of scale in larger size plants to be economically justified. Furthermore, the unexpected preferential rejection of argon versus ethylene enables the usage of the cheaper oxygen feedstock without an additional increase in the amount of ethylene lost. This is due to the higher permeation rate of argon compared to ethylene through the membrane, thus permitting the presence of substantially greater amounts of argon in the oxygen feed stream than was believed possible, yet without necessitating additional purges from the system other than in line 32. In effect, the semipermeable membrane unit not only separates $CO_2$ from the recycle gas, it also separates a substantial amount of argon as well.

Streams 28 and 34 containing the recycle gas, and fresh feed streams 38 and 40 are combined in line 4 and passed through heat exchanger 8, where it absorbs some of the heat from hot effluent stream 6 passing from the reactor 2; although a variety of other embodiments are also feasible. In any event, the hot stream enters the reactor unit, and the process can be repeated indefinitely.

The controlled oxidation reaction in the reaction zone can be carried out at temperatures ranging from about 150° to 450° C., preferably in the range from about 200°-300° C. Suitable pressures which can be employed range from about atmospheric to about 500 psia, although higher pressures can be used if so desired. Most commercial processes tend to operate in the range of 150 to 350 psia. It is of course understood that a wide variety of other embodiments than the one disclosed are suitable for use in the invention.

I claim:

1. In a process for the production of ethylene oxide which comprises:
   (a) feeding an ethylene containing stream and an oxygen feed containing 75 to 95 mole % oxygen to a reaction zone;
   (b) reacting as a gas mixture comprising 5-30 mole % ethylene and 5-9 mole % molecular oxygen in the presence of 1 to 25 mole % argon, 5 to 25 mole % $CO_2$, 0.2 to 1.0 mole % $H_2O$ and 25 to 70 mole % combined $CH_4$ and $N_2$ in a reaction zone at temperatures of 150° to 450° C. and pressures of 150-350 psia over a silver catalyst;
   (c) removing product ethylene oxide from the reaction gas mixture and;
   (d) recycling a portion of the ethylene oxide depleted stream back to (a) wherein the improvement comprises:
   (e) passing 50 to 100% of the reaction gas mixture after ethylene oxide removal to the shell side of a semipermeable membrane separation unit which efficiently and selectively extracts both $CO_2$ and argon and in which a 20 to 400 psi pressure differential is maintained between membrane sides, said selective extraction of $CO_2$ being substantially equal to the amount of $CO_2$ formed in said zone and said selective extraction of argon being substantially equal to the amount of argon entering said reaction zone in said oxygen feed;
   (f) separating a permeate stream comprising about 0.3 to 3.0 of the stream fed to the semipermeable membrane separation unit, said permeate stream being enriched in $CO_2$ and argon and containing:

(i) an amount of $CO_2$ equal to 3–25% of the $CO_2$ in the stream fed to said semipermeable membrane separation unit and substantially equal to the $CO_2$ formed in said reaction unit; and (ii) an amount of argon equal to 0.4–4.0% of the argon in the stream fed to said semipermeable membrane separation unit and substantially equal to the amount of argon entering said reaction zone in said oxygen feed; and (g) recovering a non permeate stream depleted in $CO_2$ and argon and (h) combining said non permeate stream of (g) with that portion of said reaction gas mixture, which after ethylene oxide removal is not passed to said semipermeable membrane separation unit to provide the recycle of (d).

* * * * *